United States Patent
D'Ambrogio et al.

(10) Patent No.: US 9,974,723 B2
(45) Date of Patent: *May 22, 2018

(54) ORAL CARE COMPOSITIONS COMPRISING CALCIUM CARBONATE AND SILICA

(71) Applicant: Colgate-Palmolive Company, New York, NY (US)

(72) Inventors: Robert D'Ambrogio, Princeton, NJ (US); Andrei Potanin, Hillsborough, NJ (US); Guisheng Pan, Philadelphia, PA (US); Nora Lin, Basking Ridge, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/104,244

(22) PCT Filed: Dec. 16, 2013

(86) PCT No.: PCT/US2013/075304
§ 371 (c)(1),
(2) Date: Jun. 14, 2016

(87) PCT Pub. No.: WO2015/094152
PCT Pub. Date: Jun. 25, 2015

(65) Prior Publication Data
US 2017/0014322 A1    Jan. 19, 2017

(51) Int. Cl.
| | |
|---|---|
| *A61Q 11/00* | (2006.01) |
| *A61K 8/25* | (2006.01) |
| *A61K 33/10* | (2006.01) |
| *A61K 47/38* | (2006.01) |
| *A61K 8/36* | (2006.01) |
| *A61K 8/73* | (2006.01) |
| *A61K 8/19* | (2006.01) |
| *A61K 8/24* | (2006.01) |
| *A61K 8/34* | (2006.01) |

(52) U.S. Cl.
CPC .................. *A61K 8/36* (2013.01); *A61K 8/19* (2013.01); *A61K 8/24* (2013.01); *A61K 8/25* (2013.01); *A61K 8/34* (2013.01); *A61K 8/345* (2013.01); *A61K 8/731* (2013.01); *A61Q 11/00* (2013.01); *A61K 2800/28* (2013.01); *A61K 2800/48* (2013.01); *A61K 2800/524* (2013.01); *A61K 2800/592* (2013.01)

(58) Field of Classification Search
CPC .......... A61Q 11/00; A61K 8/25; A61K 8/731; A61K 2800/48; A61K 9/2054
See application file for complete search history.

(56) References Cited

U.S. PATENT DOCUMENTS

| | | | |
|---|---|---|---|
| 5,318,773 A | 6/1994 | Winston et al. | |
| 6,042,812 A * | 3/2000 | Sanker ...................... | A61K 8/21 424/49 |
| 2003/0039617 A1 * | 2/2003 | White, Jr. .............. | A61Q 11/00 424/49 |
| 2003/0133882 A1 * | 7/2003 | Kostinko ................. | A61K 8/25 424/49 |
| 2005/0281758 A1 * | 12/2005 | Dodd ..................... | A61Q 11/00 424/49 |
| 2007/0009447 A1 | 1/2007 | Gadkari et al. | |
| 2007/0196474 A1 | 8/2007 | Withiam et al. | |
| 2009/0202451 A1 | 8/2009 | Prencipe et al. | |
| 2011/0243861 A1 * | 10/2011 | Vierling ................. | A61K 8/044 424/58 |

FOREIGN PATENT DOCUMENTS

| | | | |
|---|---|---|---|
| JP | 2003063938 A * | 3/2003 | |
| WO | WO 02/38119 | 5/2002 | |
| WO | WO 2011/147397 | 12/2011 | |
| WO | WO 2011/157497 | 12/2011 | |
| WO | WO 2011152819 A1 * | 12/2011 | ............. A01N 31/04 |
| WO | WO 2012057739 A1 * | 5/2012 | ............... A61K 8/19 |
| WO | WO 2012/143220 | 10/2012 | |
| WO | WO 2013/041419 | 3/2013 | |

OTHER PUBLICATIONS

International Search Report and Written Opinion for International Application No. PCT/US2013/075304 dated Oct. 16, 2014.

* cited by examiner

*Primary Examiner* — Tracy Liu

(57) ABSTRACT

The present invention provides an oral care composition comprising, based on the total weight of the composition: (a) 15 to 24 weight % calcium carbonate; (b) 0.9 to 2.5 weight % cellulose ether thickening agent; (c) 7 to 10 weight % thickening silica; and (d) at least 40 weight % water.

25 Claims, No Drawings

ORAL CARE COMPOSITIONS COMPRISING CALCIUM CARBONATE AND SILICA

BACKGROUND

Current calcium carbonate-based anti-cavity toothpastes typically utilize a high concentration of calcium carbonate abrasive (typically 37-42 weight %), combined with either single or dual gum systems to provide targeted therapeutic benefits and product physical stability. Water content of these formulas is typically no greater than 30 to 40 weight %.

It would be desirable to provide more cost-effective calcium carbonate-based anti-cavity toothpastes, which have acceptable cleaning efficacy, good chemical and physical stabilities, and which have desirable dispensing and ribbon characteristics.

BRIEF SUMMARY

The present invention provides an oral care composition comprising, based on the total weight of the composition: (a) 15 to 24 weight % calcium carbonate; (b) 0.9 to 2.5 weight % cellulose ether thickening agent; (c) 7 to 10 weight % thickening silica; and (d) at least 40 weight % water.

Optionally, the oral care composition comprises from 20 to 22 weight % calcium carbonate, based on the total weight of the composition. Optionally, the calcium carbonate comprises natural calcium carbonate. Optionally, the calcium carbonate comprises precipitated calcium carbonate.

Optionally, the oral care composition comprises from 8 to 9 weight % thickening silica, based on the total weight of the composition.

Optionally, the oral care composition comprises from 1 to 2 weight % cellulose ether thickening agent, based on the total weight of the composition. Optionally, the cellulose ether thickening agent comprises carboxymethylcellulose, sodium carboxymethylcellulose, hydroxymethylcellulose, hydroxyethylcellulose or derivatives thereof, hydroxypropylcellulose or derivatives thereof, hydroxypropylmethylcellulose or derivatives thereof, or mixtures thereof. Optionally, the cellulose ether thickening agent is sodium carboxymethyl cellulose. Further optionally, the oral care composition comprises the sodium carboxymethylcellulose in an amount of from 1 to 1.5 weight %, based on the total weight of the composition.

Optionally, the composition further comprises microcrystalline cellulose. Further optionally, the composition comprises from 0.4 to 0.9 weight % microcrystalline cellulose, based on the total weight of the composition. Further optionally, the ratio of microcrystalline cellulose to cellulose ether thickening agent is from 1:1 to 1:3 by weight. Still further optionally, the ratio of microcrystalline cellulose to cellulose ether thickening agent is from 1:1.5 to 1:2.75 by weight.

Optionally, the oral care composition comprises from 40 to 70 weight % water, based on the total weight of the composition. Further optionally, the oral care composition comprises at least 50 weight % water, based on the total weight of the composition.

Optionally, the ratio of calcium carbonate to thickening silica is from 1.5:1 to 3.5:1 by weight.

Optionally, the ratio of thickening silica to water is from 1:5 to 1:8.5 by weight.

Optionally, the total concentration of thickening silica and calcium carbonate is at least 27 weight %, based on the total weight of the composition.

Optionally, the oral care composition comprises 20-22 weight % calcium carbonate, 1-1.5 weight % sodium carboxymethylcellulose and 7-10 weight % thickening silica, based on the total weight of the composition. Further optionally, the oral care composition comprises about 22 weight % calcium carbonate, about 1.1 weight % sodium carboxymethylcellulose, about 8 weight % thickening silica, and about 0.4 weight % microcrystalline cellulose, based on the total weight of the composition.

Optionally, the oral care composition comprises about 20 weight % calcium carbonate, about 1.25 weight % sodium carboxymethylcellulose, and about 8 weight % thickening silica, based on the total weight of the composition.

Optionally, the oral care composition further comprises a preservative. Further optionally, the preservative is selected from benzyl alcohol and parabens. Still further optionally, the preservative is present in an amount of from 0.1 to 1 weight %, based on the total weight of the composition.

Optionally, the oral care composition further comprises a humectant. Optionally, the humectant is selected from sorbitol, glycerin, xylitol, polyethylene glycol, propylene glycol, and combinations thereof. Optionally, the humectant is sorbitol. Optionally, the humectant is glycerin. Further optionally, the humectant is present in an amount of from 5 to 20 weight %, based on the total weight of the composition.

Optionally, the composition has a pH of from 9.2 to 10.2.

Optionally, the oral care composition of further comprises a buffer system, the buffer system being: (a) a combination of sodium silicate and tetrasodium pyrophosphate; (b) a combination of sodium hydroxide, sodium bicarbonate and tetrasodium pyrophosphate; or (c) a combination of sodium bicarbonate and sodium carbonate. Further optionally, the buffer system is 0.25 to 0.75 weight % sodium silicate and 0.25 to 0.75 weight % tetrasodium pyrophosphate, based on the total weight of the composition. Further optionally, the buffer system is 0.04 to 0.5 weight % sodium hydroxide, 0.25 to 0.75 weight % sodium bicarbonate and 0.25 to 1.5 weight % tetrasodium pyrophosphate, based on the total weight of the composition.

Optionally, the composition is a toothpaste, a tooth gel, or a combination thereof.

Optionally, the viscosity of the composition is from 100,000 to 1,000,000 cps as measured at 25° C. at 1 rpm using a Brookfield Viscometer model HADV-II+Pro and a V74 spindle.

Optionally, the composition has a static yield stress of at least 50 Pa as measured at 25° C. using a Brookfield Viscometer model HADV-II+Pro and a V74 spindle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. Unless otherwise specified, all ratios expressed herein and elsewhere in the specification should be understood to refer to ratios by weight.

The present inventors have found that oral care compositions with acceptable cleaning potential, good physical and chemical stability, desirable viscosity and static yield stress, and desirable dispensing and ribbon characteristics can be obtained by formulating the compositions with specific amounts of calcium carbonate, cellulose ether thickening agent, thickening silica and water. The compositions of the present invention were also found to be more cost-effective than previous "benchmark" formulations, and have reduced specific gravity as compared to the benchmark compositions. The reduced specific gravity can provide further cost savings particularly in those geographical regions where tube filling is controlled by volume rather than by weight of the product. The reduced fill weight requires less raw material to meet inventory demands. However, the product provides the same theoretical number of brushings per tube, as consumers measure toothpaste dosage by visual dispensing (i.e. toothpaste ribbon covering toothbrush bristles) rather than by weight.

Accordingly, the present invention provides an oral care composition comprising, based on the total weight of the composition: (a) 15 to 24 weight % calcium carbonate; (b) 0.9 to 2.5 weight % cellulose ether thickening agent; (c) 7 to 10 weight % thickening silica; and (d) at least 40 weight % water.

In some embodiments, the compositions comprise the thickening silica in an amount of from 7 to 9 weight %; from 8 to 9 weight %; from 7.5 to 8.5 weight %; or about 8 weight %, based on the total weight of the composition. Examples of thickening silicas which may be used include, but are not limited to, Zeodent 165, Zeodent 163 and Zeodent 153 (from Huber); Aerosil® 200 and Sident® 22S (from Evonik); Sylodent® 15 and Perkasil® SM 660 (from W.R. Grace & Co.); and Tixocil 43B (From Rhodia).

In some embodiments, the composition comprises from 16 to 24 weight %; from 17 to 23 weight %; from 18 to 23 weight %; 20 to 22 weight %; about 22 weight %; or about 20 weight % calcium carbonate, based on the total weight of the composition. In some embodiments, the calcium carbonate is natural calcium carbonate (NCC). In other embodiments, the calcium carbonate is precipitated calcium carbonate (PCC). In some embodiments, the calcium carbonate is a combination of natural calcium carbonate and precipitated calcium carbonate. In some embodiments, the weight ratio of NCC to PCC is from 2:1 to 1:2; from 1.5:1 to 1:1.5; or about 1:1.

In some embodiments, the ratio of calcium carbonate to thickening silica is from 1.5:1 to 3.5:1 by weight; from 2:1 to 3.2:1 by weight; from 2.2:1 to 3.2:1 by weight; or about 2.5:1 by weight.

In some embodiments, the composition comprises at least 45 weight %; at least 50 weight %; at least 55 weight %; or at least 60 weight % water, based on the total weight of the composition. In some embodiments, the composition comprises from 40 to 70 weight %; from 45 to 65 weight %; or from 50 to 60 weight % water, based on the total weight of the oral care composition.

In some embodiments, the ratio of thickening silica to water is from 1:4 to 1:9; from 1:5 to 1:8.5; from 1:6 to 1:8; or about 1:7 by weight.

In some embodiments, the composition comprises from 1 to 2 weight %; from 1 to 1.75 weight %; from 1 to 1.5 weight %; from 1.1 to 1.3 weight %; about 1.25 weight %; or about 1 weight % cellulose ether thickening agent. In some embodiments, the cellulose ether thickening agent comprises carboxymethylcellulose (CMC), sodium carboxymethylcellulose (NaCMC), hydroxymethylcellulose (HMC), hydroxyethylcellulose (HEC) or derivatives thereof, hydroxypropylcellulose (HPC) or derivatives thereof, hydroxypropylmethylcellulose (HPMC) or derivatives thereof, or mixtures thereof. In some embodiments, the cellulose ether thickening agent is sodium carboxymethylcellulose. Typical commercial NaCMC options have a degree of substitution (DS) of from 0.7 to 1.2 (i.e. for every 10 anhydroglucose units, 7 to 12 hydroxy groups will be substituted with carboxymethyl groups). In general, CMC becomes more hydrophilic with increasing DS level, and the performance of the gum is modified with different DS. For the compositions of the present invention, NaCMC with degrees of substitution from 0.7 (Type 7) to 1.2 (Type 12) may be used. Particular examples of sodium carboxymethylcellulose which may be used in the present invention include NaCMC Type 7 (such as Gelycel® from Amtex Chemicals, LLC) and NaCMC Type 8 (such as CMC-TMS from Chongqing Lihong Fine Chemical Co. Ltd.). In some embodiments, the NaCMC is present in the composition in an amount of from 1 to 2 weight %; from 1 to 1.75 weight %; from 1 to 1.5 weight %, from 1.05 to 1.3 weight %; from 1.1 to 1.3 weight %; about 1.25 weight %, or about 1 weight %.

In some embodiments, the composition further comprises microcrystalline cellulose (MCC). An example of a source of MCC is Avicel® (FMC Corporation), which contains MCC in combination with NaCMC. Both Avicel® RC-591 (MCC containing 8.3 to 13.8 weight % NaCMC) and Avicel® CL-611 (MCC containing 11.3 to 18.8 weight % NaCMC) are suitable for use in the compositions of the present invention, although Avicel® CL-611 is preferred due to its greater ease of processing/dispersing. In certain embodiments, the microcrystalline cellulose is present in an amount of from 0.3 to 1 weight %; from 0.4 to 0.9 weight %; or from 0.44 to 0.81 weight %, based on the total weight of the composition. In certain embodiments, the ratio of microcrystalline cellulose to cellulose ether thickening agent is from 1:1 to 1:3 by weight; or from 1:1.5 to 1:2.75 by weight. In any of the above embodiments comprising microcrystalline cellulose, the cellulose ether thickening agent may be sodium carboxymethylcellulose. In certain such embodiments, the sodium carboxymethylcellulose may be present in an amount of from 1 to 1.5 weight %; from 1.05 to 1.3 weight %; or from 1.05 to 1.2 weight % based on the total weight of the composition.

In some embodiments, the total concentration of thickening silica and calcium carbonate is at least 27 weight %, based on the total weight of the composition. In some embodiments, the total concentration of calcium carbonate and thickening silica is from 27 to 38 weight %; from 27 to 35 weight %; from 27 to 30 weight %; from 27 to 29 weight %; from 27 to 28 weight %; or about 27 weight %.

In some embodiments, the oral care composition comprises 20-22 weight % calcium carbonate, 1-1.5 weight % sodium carboxymethylcellulose and 7-10 weight % thickening silica. In some embodiments, with 20-22 weight % calcium carbonate, 1-1.5 weight % NaCMC and 7-10 weight % thickening silica, the oral care composition further comprises from 0.4 to 0.9 weight % microcrystalline cellulose. In some embodiments, the oral care composition comprises about 22 weight % calcium carbonate, about 1.1 weight % sodium carboxymethylcellulose, about 8 weight % thickening silica, and about 0.4 weight % microcrystalline cellulose.

In some embodiments, the oral care composition comprises about 20 weight % calcium carbonate, about 1.25 weight % sodium carboxymethylcellulose, and about 8 weight % thickening silica.

In some embodiments, the compositions of the present invention also comprise an antibacterial or preservative agent, such as benzyl alcohol or parabens such as methylparaben or propylparaben. In some embodiments, the preservative is benzyl alcohol. The antibacterial or preservative agent may be present in the composition in an amount of from 0.1 to 1 weight %; 0.2 to 0.5 weight %; or about 0.3 weight % by total weight of the composition.

In some embodiments, the oral care compositions further comprise a humectant. In certain embodiments, the humectant is selected from sorbitol, glycerin, xylitol, polyethylene glycol, propylene glycol, and combinations thereof. In some embodiments, the humectant is glycerin. In some embodiments, the humectant is sorbitol, In certain embodiments, the humectant is present in the composition in an amount of from 5 to 20 weight %; from 7 to 17 weight %; or from 8 to 13 weight %; or from 9 to 10 weight %, based on the total weight of the composition. In some embodiments, the weight ratio of humectant to cellulose ether structuring agent is from 7:1 to 16:1; from 9:1 to 13:1; or about 9:1. When the humectant is supplied as a solution in water, for example sorbitol as a 70 weight % solution in water, the amount of humectant is calculated as the active weight of the humectant, e.g. for a composition comprising 25 weight % sorbitol (as 70 weight % aqueous solution), the concentration of humectant is 17.5 weight %.

In some embodiments, the composition has a pH of from 8.5 to 10.5; or from 9.2 to 10.2. In certain embodiments, the composition comprises a buffer system, which may be: (a) a combination of sodium silicate and tetrasodium pyrophosphate; (b) a combination of sodium hydroxide, sodium bicarbonate and tetrasodium pyrophosphate; or (c) a combination of sodium bicarbonate and sodium carbonate. In some embodiments, the buffer system is 0.25 to 0.75 weight % sodium silicate and 0.25 to 0.75 weight % tetrasodium pyrophosphate; or about 0.4 weight % sodium silicate and 0.5 weight % tetrasodium pyrophosphate, based on the total weight of the composition. Various grades of sodium silicate are characterized by their $SiO_2:Na_2O$ ratio, which can vary between 1:2 and 1:3.75 by weight. Grades with this ratio being greater than 1:2.85 by weight are termed "alkaline". An example of a sodium silicate useful in the present invention is sodium silicate with target pH of 8.5, which has a $SiO_2:Na_2O$ ratio of 1:3.26 by weight and a relative density of 41 BE (BE denoting "Baume") and is denoted as "sodium silicate 1:3.26-41 BE".

In some embodiments, the buffer system is 0.04 to 0.5 weight % sodium hydroxide, 0.25 to 0.75 weight % sodium bicarbonate and 0.25 to 1.5 weight % tetrasodium pyrophosphate; or about 0.12 weight % sodium hydroxide, about 0.25 weight % sodium bicarbonate and about 1.25 weight % tetrasodium pyrophosphate; or about 0.06 weight % sodium hydroxide, about 0.5 weight % sodium bicarbonate and about 0.5 weight % tetrasodium pyrophosphate based on the total weight of the composition. In some embodiments, the buffer system is 0.05 to 0.5 weight % sodium bicarbonate and 0.2 to 0.6 weight % sodium carbonate; or about 0.1 weight % sodium bicarbonate and 0.4 weight % sodium carbonate, based on the total weight of the composition.

In some embodiments, the oral care composition does not contain talc. In some embodiments, the oral care composition does not contain a clay thickening agent. In some embodiments, the oral care composition does not contain talc or a clay thickening agent.

In some embodiments, the oral care composition is a toothpaste, a tooth gel, or a combination thereof.

In some embodiments, the viscosity of the oral care composition is from 100,000 to 1,000,000; from 180,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition immediately following its formation is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 1 day (24 hours) at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 3 days at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 1 week at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 1 month at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle. In some embodiments, the viscosity of the oral care composition after storing for 2 months at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-H+Pro and a V74 spindle. In some embodiments, the viscosity of the oral care composition after storing for 3 months at 25° C./60% relative humidity (RH) in a sealed 5 fl. oz. laminate tube is from 100,000 to 1,000,000; from 190,000 to 800,000 cps; from 200,000 to 800,000 cps; from 200,000 to 700,000 cps; from 300,000 to 600,000 cps; or from 300,000 to 500,000 cps, as measured at 25° C. at 1 rpm using a Brookfield Viscometer Model HADV-II+Pro and a V74 spindle.

In some embodiments, the composition has a static yield stress (YS) of at least 50 Pa; from 50 to 400 Pa; or from 80 to 300 Pa, as measured at 25° C. using a Brookfield Viscometer Model HADV-II+Pro and a V74 spindle. In some embodiments, the static yield stress of the composition immediately following its formation is at least 50 Pa; from 50 to 400 Pa; or from 80 to 220 Pa, as measured at 25° C. using a Brookfield Viscometer Model HADV-II+Pro and a V74 spindle. In some embodiments, the composition has a static yield stress of at least 50 Pa; from 50 to 400 Pa; or from 80 to 220 Pa, as measured at 25° C. using a Brookfield Viscometer Model HADV-II+Pro and a V74 spindle, after storing for 1 day (24 hours) at 25° C./60% relative humidity (RH) in a sealed 5 fl. oz. laminate tube. In some embodiments, the composition has a static yield stress of at least 50 Pa; from 50 to 400 Pa; from 80 to 300 Pa; or from 90 to 290 Pa, as measured at 25° C. using a Brookfield Viscometer Model HADV-II+Pro and a V74 spindle after storing for 3 days at 25° C./60% relative humidity (RH) in a sealed 5 fl. oz. laminate tube. In sonic embodiments, the composition has a static yield stress of at least 50 Pa; from 50 to 400 Pa; or from 80 to 320 Pa, as measured at 25° C. using a Brookfield Viscometer Model HADV-II+Pro and a V74 spindle, after storing for 1 week at 25° C./60% relative humidity (RH) in a sealed 5 fl. oz. laminate tube. In some embodiments, the composition has a static yield stress of at least 50 Pa; from 100 to 320 Pa; or from 150 to 315 Pa, as measured at 25° C. using a Brookfield. Viscometer Model HADV-II+Pro and a V74 spindle, after storing for 1 month at 25° C./60% relative humidity (RH) in a sealed 5 fl oz. laminate tube. In some embodiments, the composition has a static yield stress of at least 50 Pa; from 100 to 350 Pa; from 150 to 330 Pa; or from 180 to 330 Pa, as measured at 25° C. using a Brookfield Viscometer Model HADV-II+Pro and a V74 spindle, after storing for 2 months at 25° C./60% relative humidity (RH) in a sealed 5 fl. oz. laminate tube. In some embodiments, the composition has a static yield stress of at least 50 Pa; from 200 to 330 Pa; or from 220 to 330 Pa, as measured at 25° C. using a Brookfield Viscometer Model HADV-II+Pro and a V74 spindle, after storing for 3 months at 25° C./60% relative humidity (RH) in a sealed 5 fl. oz. laminate tube.

The oral care compositions of the present invention may further comprise additional ingredients. These additional ingredients may include, but are not limited to, diluents, bicarbonate salts, surfactants, foam modulators, sweeteners, flavorants, pigments, antibacterial agents, anticaries agents, anticalculus or tartar control agents, and mixtures thereof.

In some embodiments, the oral care compositions of the present invention comprise at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of about 0.1 wt. % to about 50 wt. %, for example about 1 wt. % to 20 wt. %, by total weight of the composition.

The oral care compositions of the invention may also comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the composition.

The oral care compositions of the invention may comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000 000, for example 500,000 to 5,000,000, or 1,000,000 to 2,500,000. One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition.

The oral care compositions of the present vention may comprise at least one sweetener (such as, for example, sodium saccharin), useful for example to enhance taste of the composition. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

The compositions of the present invention may also comprise at least one flavorant, useful for example to enhance taste of the composition. Any orally acceptable natural or synthetic flavorant can be used, including without limitation tea flavours, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt. % to about 5 wt. %, for example, from about 0.03 wt. % to about 2.5 wt. %, optionally about 0.05 wt. % to about 1.5 wt.

%, further optionally about 0.1 wt. % to about 0.3 wt. % by total weight of the composition.

The compositions of the invention may comprise at least one colorant. Colorants herein include pigments, dyes, lakes and agents imparting a particular luster or reflectivity such as pearling agents. Any orally acceptable colorant can be used, including without limitation titanium dioxide, zinc oxide, red, yellow, brown and black iron oxides, ferric ammonium ferrocyanide, manganese violet, ultramarine, titaniated mica, bismuth oxychloride, and the like. One or more colorants are optionally present in a total amount of from about 0.001 wt. % to about 20 wt. %, for example, from about 0.01 wt. % to about 10 wt. %, or from about 0.1 wt. % to about 5 wt. %, by total weight of the composition.

The oral care compositions may also comprise a fluoride ion source. Fluoride ion sources include, but are not limited to: stannous fluoride, sodium fluoride, potassium fluoride, potassium monofluorophosphate, sodium monofluorophosphate (NaMFP), ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The compositions of the present invention may comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention may include antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt. % to about 20 wt. % by weight based on the total weight of the composition, depending on the agent chosen.

The composition of the invention may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention may additionally optionally comprise a tartar control (anticalculus) agent as provided below. Tartar control agents among those useful herein include salts of the specified agents, including alkali metal and ammonium salts. The agents include: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

EXAMPLES

Example 1

Formulations containing different loading of calcium carbonate abrasive were compared for mechanical cleaning potential by means of in vitro pellicle cleaning ratio (PCR) scores. An in vitro model has been developed for evaluating the ability of dentifrices to clean extrinsic (surface) stains. Through use of a stained film deposited on enamel sections, a comparison of test formulations to a standard ADA (American Dental Association) abrasion reference material (slurry of calcium pyrophosphate) can be established. The ratio of the test formulation to the standard is the pellicle cleaning ratio (PCR). (Reference: Stookey, G. K. et al, "In vitro removal of stain with dentifrices", Journal of Dental Research, Vol. 61, no. 11, November 1982, p. 1236-1239).

The different formulations tested (Formulas A to E, and a "Benchmark" comparative formula) are detailed below in Table 1, with the PCR scores obtained (using the method as described above) for each of these formulations being shown in Table 2:

TABLE 1

Dentifrice formulations with different calcium carbonate loading.

| | Formula | | | | | |
|---|---|---|---|---|---|---|
| | A | B | C | D | E | Benchmark #1 |
| Ppt. Calcium Carbonate - PCC | 10.00 | 20.00 | 10.00 | 0.00 | 30.00 | 40.00 |
| Nat. Calcium Carbonate - NCC | 0.00 | 0.00 | 10.00 | 20.00 | 0.00 | 0.00 |
| Thickener Silica | 12.00 | 8.00 | 8.00 | 8.00 | 4.00 | 0.00 |
| NaCMC Type 7/500T | 1.00 | 1.00 | 1.15 | 1.15 | 1.10 | 0.80 |
| Sorbitol, Non Crystallizing (70 wt. % aq soln) | 13.00 | 13.00 | 13.00 | 13.00 | 0.00 | 20.00-30.00 |
| Glycerin, vegetable - USP | 0.00 | 0.00 | 0.00 | 0.00 | 16.10 | 0.00 |
| Tetrasodium Pyrophosphate | 0.50 | 0.50 | 0.50 | 0.50 | 0.50 | 0.25-0.75 |
| Sodium Silicate (1:3.26-41BE) | 0.40 | 0.40 | 0.40 | 0.40 | 0.40 | 0.25-0.75 |
| NaMFP - USP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.25 | 0.25 | 0.25 | 0.25 | 0.25 | 0.10-1.00 |
| Flavor | 0.95 | 0.95 | 0.95 | 0.95 | 0.95 | 0.95 |
| Benzyl Alcohol | 0.30 | 0.30 | 0.30 | 0.30 | 0.30 | 0.10-1.00 |
| Demineralized Water | 58.74 | 52.74 | 52.59 | 52.59 | 43.54 | 25.00-35.00 |

TABLE 2

PCR scores for dentifrice formulations of Table 1
(PCR scores with the same superscript letter are not
significantly different, as per ANOVA (Analysis of
Variance) and SNK (Student-Newman-Keuls) analyses)

| | Formula | | | | | |
|---|---|---|---|---|---|---|
| | A | B | C | D | E | Benchmark #1 |
| Ppt. Calcium Carbonate - PCC | 10.00 | 20.00 | 10.00 | 0.00 | 30.00 | 40.00 |
| Nat. Calcium Carbonate - NCC | 0.00 | 0.00 | 10.00 | 20.00 | 0.00 | 0.00 |
| PCR Score* | 72[b] | 80[a] | 83[a] | 85[a] | 80[a] | 80[a] |

The PCR scores for formulations containing a total of 10 weight %, 20 weight %, 30 weight % and 40 weight % calcium carbonate (as PCC and/or NCC) were evaluated, as shown in Table 2.

It was found that, of the formulations tested, a minimum calcium carbonate concentration of 20 weight % was required in order to deliver effective mechanical cleaning of teeth. The PCR scores for the compositions containing a total of 20 weight %, 30 weight % and 40 weight % were not significantly different (see Table 2, above). Compositions formulated with 20 weight % calcium carbonate as either PCC alone, NCC alone, or as a combination of PCC and NCC provided statistically equivalent cleaning potential to the "benchmark" formulation, which contained 40 weight % PCC.

Based on these PCR results, further studies were conducted upon compositions containing approximately 20 weight % calcium carbonate abrasives in order to determine optimal balance of thickener silica and cellulose ether thickening agent levels.

Example 2

The rheology characteristics of the "benchmark" formula are largely dictated by the combination of high calcium carbonate loading with the low concentration of cellulose gum. However, the present inventors have discovered that, for acceptable product stability, bulk product transfer behavior during manufacturing and desirable consumer related attributes such as product dispensing (from a tube) and ribbon quality/standup, further structuring agents are required in combination with cellulose gum in the high water-content/reduced calcium carbonate-content compositions of the present invention.

The present inventors have discovered that the viscosity and static yield stress (YS) profiles of the compositions of the present invention can be adjusted so as to be close to those of the "benchmark" product by balancing the concentration of thickener silica and cellulose gum in the compositions. Static YS is defined as the lowest shear stress needed to break the sample structure and start flow and is a key attribute in quantifying toothpaste ribbon quality. It is also a contributing factor in toothpaste dispensing characteristics and physical stability.

Tables 3 and 4 demonstrate the impact of increasing levels of thickener(with all other structuring agents held at a constant concentration), while Tables 5 and 6 demonstrate the impact of increasing levels of sodium carboxymethylcellulose (with the concentrations of the other formula components being held constant).

The viscosity of compositions F to O (and the "Benchmark" formulation) in Tables 3 and 5 was measured immediately after their formation ("initial"), and again after 1 day of storage, 3 days of storage, 1 week of storage, 1 month of storage, 2 months of storage and 3 months of storage (as shown in Tables 4 and 6). The storage conditions were 25° C. and 60% relative humidity (RH), and the compositions were stored in sealed 5 fl. oz. laminate tubes with the tubes filled to capacity. The viscosity measurements were made using a Brookfield Viscometer model HADV-II+Pro and a V74 spindle, at 1 rpm and at 25° C. Compositions with viscosity of from 100,000 to 1,000,000 cps at all time points tested are preferred.

The static yield stress (YS) of the above compositions was also measured immediately after their formation ("initial"), and again after 1 day, 3 days, 1 week, 1 month, 2 months and 3 months of storage at 25° C. and 60% relative humidity, and at 40° C./75% relative humidity, with the compositions being stored in sealed 5 fl. oz. laminate tubes with the tubes filled to capacity. The results fir the measurements at 25° C. and 60% relative humidity are reported in Tables 4 and 6, below. The static yield stress measurements were made using a Brookfield Viscometer model HADV-II+Pro and a V74 spindle, at 25° C. A yield stress of approximately 50 Pa or greater is desirable in order to maintain sufficient physical stability, and a yield stress of approximately 50-400 Pa provides desirable toothpaste ribbon quality.

The viscosity and static yield stress were measured on a Brookfield HADVII+Pro viscometer with spindle V-74 available from Brookfield Engineering Laboratories. All measurements on this viscometer were performed at room temperature (25° C.). In the tests, the spindle is rotated at a pre-set RPM (rotations per minute) series, while torque (Torque %) is reported in terms of % of its maximum (Tmax) as specified for the instrument (Tmax=1.437 mN·m for HADVII+Pro). Only those measurements with Torque % between 10 and 100% of Tmax are valid. The raw data (Torque % and RPM) were converted into shear stress (SS) and shear rate (SR) using well known formulas for Couette geometry, assuming that the vane (spindle) performs as its encompassing cylinder (i.e., assuming that paste between its blades move as a solid piece):

$$SR = SRC * RPM$$

$$SS = SF * \text{Torque \%}$$

where $$SRC = (\pi/15)C/(1-x^2)$$

$$SF = 0.01 * T\max * C/(2\,\pi L R^2)$$

$$C = (1+x^2)/2,$$

where L is the vane blade length and R is the vane radius; and x is the ratio of spindle diameter to the diameter of the vessel in which the measurement is performed. (* denotes multiplication). Here L and R are in meters, Tmax is in N·m, SS is in Pascals and SR is in reciprocal seconds.

In the test, RPM was swept from 0.5 to 200 in 20 steps in logarithmical mode, 10 sec per step. "Viscosity" reported herein refers to SS/SR at 1 RPM (reported herein in centipoise, i.e. cps, wherein 1 cps=0.001 Pa·s). Furthermore, SS(SR) function was fitted with Casson equation, $SS=(Y''+(V0*SR)^n)^{1/n}$ where Y, V0 and n are fitting parameters. Only the monotonously increasing section of the curve bended upward (i.e., the one in which both first and second derivative of SS(SR) were positive, typically above 1 RPM) was fitted. "Yield stress" reported herein refers to Y parameter.

A "Separation Score" was also obtained for each of Formulas F to O (and the Benchmark formulation), and is shown in Tables 4 and 6, below. This Separation Score is an indication of the physical stability of the compositions, and is obtained from a visual assessment which was conducted on each sample after three months accelerated aging at 40° C. (105° F.) and 75% relative humidity. This high-temperature aging is used as a predictive measure, and has been found to correlate well with two years' shelf-life determination under 25° C./60% relative humidity conditions. In these evaluations, a trained evaluator visually examines several attributes of the compositions under test, and provides a numeric rating of 0 to 4 (0=no separation; 1=slight separation; 2=minor; 3=moderate; 4=severe) for each attribute for each time point and for each set of storage conditions. The attributes are measured for: (1) a ribbon of the toothpaste squeezed from the tube (ribbon stand-up, cap separation, aeration, lumps/grit, graininess, discoloration); (2) tube cut open (appearance, aeration, separation, wall separation, clip separation, pocket, discoloration). The composition passes this visual inspection test if it achieved a rating of 3 or less in all of the indicated attributes. The average score specifically related to wall separation across at least three tubes for each formulation is reported in the Tables below (as the "Separation Score"), with a score of three or less being acceptable ("pass") and a score of greater than three being unacceptable ("fail").

TABLE 3

Formulas with 20% PCC, 1.25% CMC and different levels of thickener silica

| | Formula | | | | | |
|---|---|---|---|---|---|---|
| | F | G | H | I | J | Benchmark #1 |
| Ppt. Calcium Carb. - PCC | 20.00 | 20.00 | 20.00 | 20.00 | 20.00 | 40.00 |
| Thickener Silica | 6.00 | 7.00 | 8.00 | 9.00 | 10.00 | 0.00 |
| NaCMC Type 7/500T | 1.25 | 1.25 | 1.25 | 1.25 | 1.25 | 0.80 |
| Sorbitol, N.C. (70 wt. % aq soln) | 13.00 | 13.00 | 13.00 | 13.00 | 13.00 | 20.00-30.00 |
| Tetrasodium Pyrophosphate | 0.50 | 0.50 | 0.50 | 0.50 | 0.50 | 0.25-0.75 |
| Sodium Silicate (1:3.26-41BE) | 0.40 | 0.40 | 0.40 | 0.40 | 0.40 | 0.25-0.75 |
| Demineralized Water | 54.49 | 53.49 | 52.49 | 51.49 | 50.49 | 25.00-35.00 |
| NaMFP - USP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.25 | 0.25 | 0.25 | 0.25 | 0.25 | 0.10-1.00 |
| Flavor | 0.95 | 0.95 | 0.95 | 0.95 | 0.95 | 0.95 |
| Benzyl Alcohol | 0.30 | 0.30 | 0.30 | 0.30 | 0.30 | 0.10-1.00 |

TABLE 4

Viscosity (×10,000 cps)/YS (Pa) @ RT, V74 spindle of Formulas F to J

| | Formula | | | | | |
|---|---|---|---|---|---|---|
| | F | G | H | I | J | Benchmark #1 |
| Viscosity (×10,000 cps)/YS (Pa) @ RT, V74 spindle | | | | | | |
| Initial | 17/57 | 33/85 | 36/155 | 48/205 | 43/219 | 24/128 |
| 1 day | 19/57 | 38/123 | 44/220 | 56/235 | 85/219 | 41/290 |

TABLE 4-continued

Viscosity (×10,000 cps)/YS (Pa) @ RT, V74 spindle of Formulas F to J

| | Formula | | | | | |
|---|---|---|---|---|---|---|
| | F | G | H | I | J | Benchmark #1 |
| 3 days | 28/57 | 38/129 | 45/290 | 55/255 | 128/229 | 44/290 |
| 1 Week | 28/85 | 37/193 | 43/290 | 64/290 | 171/229 | 47/319 |
| 1 Month | 29/85 | 35/215 | 46/290 | 59/290 | 220/290 | 56/353 |
| 2 Months | 29/85 | 37/215 | 50/290 | 66/290 | 220/335 | 58/353 |
| 3 Months | 29/85 | 37/215 | 51/290 | 68/290 | 228/335 | 58/353 |
| Separation Score | | | | | | |
| | 3.57 (Fail) | 3.00 (Pass) | 2.75 (Pass) | 2.70 (Pass) | 2.53 (Pass) | 2.68 (Pass) |

TABLE 5

Formulas with 20% PCC, 8% Thickener Silica and different levels of CMC

| | Formula | | | | | |
|---|---|---|---|---|---|---|
| | K | L | M | N | O | Benchmark #1 |
| Ppt. Calcium Carb. - PCC | 20.00 | 20.00 | 20.00 | 20.00 | 20.00 | 40.00 |
| Limestone - NCC | 0.00 | 0.00 | 0.00 | 0.00 | 0.00 | 0.00 |
| Thickener Silica | 8.00 | 8.00 | 8.00 | 8.00 | 8.00 | 0.00 |
| NaCMC Type 7/500T | 0.70 | 0.90 | 1.10 | 1.30 | 1.50 | 0.80 |
| Sorbitol, N.C. (70 wt. % aq soln) | 13.00 | 13.00 | 13.00 | 13.00 | 13.00 | 20.00-30.00 |
| Glycerin, vegetable - USP | 0.00 | 0.00 | 0.00 | 0.00 | 0.00 | 0.00 |
| Tetrasodium Pyrophosphate | 0.50 | 0.50 | 0.50 | 0.50 | 0.50 | 0.25-0.75 |
| Sodium Hydroxide (50 wt. % aq soln) | 0.00 | 0.00 | 0.00 | 0.00 | 0.00 | 0.00 |
| Sodium Bicarbonate | 0.00 | 0.00 | 0.00 | 0.00 | 0.00 | 0.00 |
| Sodium Silicate (1:3.26-41BE) | 0.40 | 0.40 | 0.40 | 0.40 | 0.40 | 0.25-0.75 |
| Demineralized Water | 53.04 | 52.84 | 52.64 | 52.44 | 52.24 | 25.00-35.00 |
| NaMFP - USP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.25 | 0.25 | 0.25 | 0.25 | 0.25 | 0.10-1.00 |
| Flavor | 0.95 | 0.95 | 0.95 | 0.95 | 0.95 | 0.95 |
| Benzyl Alcohol | 0.30 | 0.30 | 0.30 | 0.30 | 0.30 | 0.10-1.00 |

TABLE 6

Viscosity and separation score of Formulas K to O

| | Formula | | | | | |
|---|---|---|---|---|---|---|
| | K | L | M | N | O | Benchmark #1 |
| Viscosity (×10,000 cps)/YS (Pa) @ RT, V74 spindle | | | | | | |
| Initial | 11/29 | 18/52 | 21/105 | 42/142 | 71/162 | 24/128 |
| 1 day | 12/29 | 21/52 | 29/128 | 48/142 | 89/205 | 41/290 |
| 3 days | 12/29 | 23/66 | 33/126 | 48/162 | 121/277 | 44/290 |
| 1 Week | 19/37 | 29/63 | 30/137 | 53/233 | 156/290 | 47/319 |
| 1 Month | 22/35 | 31/65 | 43/137 | 58/262 | 190/325 | 56/353 |
| 2 Months | 28/35 | 34/63 | 40/139 | 52/290 | 210/310 | 58/353 |
| 3 Months | 29/35 | 32/63 | 42/144 | 55/290 | 221/315 | 58/353 |

TABLE 6-continued

Viscosity and separation score of Formulas K to O

| Formula | | | | | |
|---|---|---|---|---|---|
| K | L | M | N | O | Bench-mark #1 |
| Separation Score | | | | | |
| 3.68 (Fail) | 2.96 (Pass) | 2.68 (Pass) | 2.64 (Pass) | 2.41 (Pass) | 2.68 (Pass) |

It was found that thickener silica primarily influences product viscosity, with some contribution to YS properties. NaCMC was found to contribute to both yield stress and viscosity properties even at relatively low concentrations.

Both thickener silica and NaCMC aid product physical stability of the high water compositions of the present invention. Without wishing to be bound by any theory, it is believed that this can be partly attributed to the ability of these materials to efficiently bind free water.

As can be seen from the Separation Scores obtained in Table 4, the composition comprising 6 weight % thickener silica did not have acceptable physical stability (Separation Score of 3.57, which is classed as a "Fail"). However, the compositions containing 7 weight %, 8 weight %, 9 weight % and 10 weight % thickener silica all gave Separation Scores of 3 or less, indicating acceptable physical stability.

As can be seen from the Separation Scores obtained in Table 6 (in which each of the compositions—with the exception of the "Benchmark"—contained 8 weight % silica), the composition containing 0.7 weight % NaCMC did not have acceptable physical stability (Separation Score of 3.68, which is classed as a "Fail"). However, the compositions containing 0.9 weight %, 1.10 weight %, 1.30 weight % and 1.50 weight % NaCMC all gave separation scores of less than 3, indicating acceptable physical stability.

The results obtained above indicate that formulations containing 7-10 weight % thickener silica, 1.0-1.50 weight % NaCMC and 20-22 weight % PCC provided suitable product stability. Furthermore, a combination of 8 weight % thickener silica, about 1.25 weight % NaCMC and 20 weight % calcium carbonate abrasive provides the closest match to the benchmark product in terms of viscosity and static yield stress.

Example 3

Compositions were also prepared with utilized either all-sorbitol or all-glycerin humectant, in combination with either precipitated calcium carbonate (PCC) or natural calcium carbonate (NCC) abrasive (as shown in Table 7, below).

The viscosity, yield stress and Separation Score of these compositions were measured using the same methods/protocols as described in Example 1, above.

The concentration of soluble fluoride ion (in ppm) present in the compositions, and the pH of a 10 weight % solution of the compositions in deionized water, were measured immediately after the formation of the compositions, and again after three months aging in sealed 5 fl. oz. tubes (filled to capacity) at controlled room temperature (25° C. and 60% relative humidity) and accelerated high temperature conditions (40° C. and 75% relative humidity), in order to evaluate the chemical stability of the formulations.

The specific gravity of the formulations was also measured immediately after the formation of the compositions.

A gravimetric method was utilized where a cylinder of known mass and volume was filled to capacity with the test product. The cylinder filled with test product was then weighed and the mass of the cylinder was then subtracted from the total mass to obtain the mass of the test product. The mass of the test product (in grams) was then divided by the volume of the cylinder (in milliliters) to obtain the specific gravity of the test product. The measurement was done at 25° C. and atmospheric pressure. The specific gravity of the formulations is reported herein as the specific gravity in relation to water, which has a specific gravity of 1 when measuring mass in grams and volume in milliliters (cubic centimeters) at 25° C. and atmospheric pressure.

The results are shown in Table 8, below.

TABLE 7

Optimized High Water Formulas containing Calcium Carbonate & Thickener Silica

| | Formula | | | | | |
|---|---|---|---|---|---|---|
| | P | Q | R | S | T | Benchmark #1 |
| Ppt. Calcium Carbonate - PCC | 20.00 | 22.00 | 22.00 | 22.00 | 0.00 | 40.00 |
| Nat. Calcium Carbonate - NCC | 0.00 | 0.00 | 0.00 | 0.00 | 20.00 | 0.00 |
| Thickener Silica | 8.00 | 8.00 | 9.00 | 7.00 | 8.00 | 0.00 |
| NaCMC Type 7/500T | 1.25 | 1.25 | 1.00 | 1.50 | 0.00 | 0.80 |
| NaCMC Type 8 | 0.00 | 0.00 | 0.00 | 0.00 | 1.30 | 0.00 |
| Sorbitol, N.C. (70 wt. % aq soln) | 13.00 | 0.00 | 0.00 | 13.00 | 13.00 | 20.00-30.00 |
| Glycerin, vegetable - USP | 0.00 | 9.10 | 9.10 | 0.00 | 0.00 | 0.00 |
| Refined Soda Ash | 0.00 | 0.00 | 0.00 | 0.00 | 0.90 | 0.00 |
| Tetrasodium Pyrophosphate | 0.50 | 0.50 | 0.50 | 0.50 | 0.00 | 0.25-0.75 |
| Sodium Hydroxide (50 wt. % aq soln) | 0.00 | 0.00 | 0.12 | 0.12 | 0.00 | 0.00 |
| Sodium Bicarbonate | 0.00 | 0.00 | 0.50 | 0.50 | 0.10 | 0.00 |
| Sodium Silicate (1:3.26-41BE) | 0.40 | 0.40 | 0.00 | 0.00 | 0.00 | 0.25-0.75 |
| Demineralized Water | 52.59 | 54.49 | 53.60 | 51.20 | 52.59 | 25.00-35.00 |
| NaMFP-USP | 1.10 | 1.10 | 1.10 | 1.10 | 1.10 | 1.00-1.50 |
| Sodium Lauryl Sulfate | 1.76 | 1.76 | 1.76 | 1.76 | 1.76 | 1.00-2.00 |
| Sodium Saccharin | 0.25 | 0.25 | 0.25 | 0.25 | 0.15 | 0.10-1.00 |
| Flavor | 0.85 | 0.85 | 0.85 | 0.85 | 0.80 | 0.95 |
| Benzyl Alcohol | 0.30 | 0.30 | 0.30 | 0.30 | 0.30 | 0.10-1.00 |

TABLE 8

Viscosity, pH, soluble F−, specific gravity and separation score of Formulas P to T

| | Formula | | | | | |
|---|---|---|---|---|---|---|
| | P | Q | R | S | T | Benchmark #1 |
| Viscosity (×10,000 cps)/YS (Pa) @ RT, V74 spindle | | | | | | |
| Initial | 36/155 | 32/142 | 46/85 | 22/212 | 26/185 | 24/128 |
| 1 day | 44/220 | 35/142 | 44/85 | 28/212 | 28/195 | 41/290 |
| 3 days | 45/290 | 38/162 | 49/96 | 31/229 | 33/229 | 44/290 |
| 1 Week | 43/290 | 44/180 | 56/85 | 41/229 | 34/315 | 47/319 |
| 1 Month | 46/290 | 57/215 | 62/152 | 38/229 | 45/315 | 56/353 |
| 2 Months | 50/290 | 64/235 | 60/185 | 47/315 | 52/329 | 58/353 |
| 3 Months | 51/290 | 58/235 | 66/222 | 44/315 | 50/329 | 58/353 |

TABLE 8-continued

Viscosity, pH, soluble F⁻, specific gravity and separation score of Formulas P to T

| | Formula | | | | | |
|---|---|---|---|---|---|---|
| | P | Q | R | S | T | Benchmark #1 |
| pH (10% in water) | | | | | | |
| Initial | 9.52 | 9.55 | 9.59 | 9.57 | 9.54 | 9.61 |
| 3 months @ 25° C./60% RH | 9.49 | 9.50 | 9.44 | 9.49 | 9.50 | 9.61 |
| 3 months @ 40° C./75% RH | 9.41 | 9.39 | 9.37 | 9.41 | 9.46 | 9.60 |
| Soluble F⁻, ppm | | | | | | |
| Initial | 1445 | 1435 | 1432 | 1440 | 1445 | 1455 |
| 3 months @ 25° C./60% RH | 1218 | 1109 | 1115 | 1012 | 1110 | 1038 |
| 3 months @ 40° C./75% RH | 977 | 946 | 927 | 915 | 970 | 913 |
| Specific Gravity | | | | | | |
| | 1.28 | 1.28 | 1.29 | 1.29 | 1.33 | 1.45 |
| Separation Score | | | | | | |
| | 2.75 (Pass) | 2.71 (Pass) | 2.86 (Pass) | 2.64 (Pass) | 2.16 (Pass) | 2.68 (Pass) |

The three month aging evaluations (pH and soluble fluoride concentration) confirmed that Formulations P to T had acceptable chemical and physical stability. It was found that formula pH should be targeted with the range of from 9.2 to 10.2, in order to ensure chemical stability of the calcium carbonate-containing formulas. The combinations of 1) sodium silicate and tetrasodium pyrophosphate or 2) sodium hydroxide, sodium bicarbonate and tetrasodium pyrophosphate or 3) sodium carbonate and sodium bicarbonate were found to be effective buffer systems for these formulas. Addition of benzyl alcohol to these high water formulations also ensures sufficient robustness to potential microbial contamination.

As shown above, the compositions of the present invention (with reduced level of abrasives and partial substitution of low density thicker silica in place of higher density PCC or NCC, as compared to the Benchmark formula) provide toothpaste of significantly reduced specific gravity as compared to the benchmark. The reduced specific gravity can provide additional formula savings in regions where product containers are filled and marketed by volume rather than by weight of product. The reduced fill weight requires less raw material/product manufacturing to meet inventory demands. However, the product provides the same theoretical number of brushings per tube since consumers measure by visual dispensing (ribbon length approximately covers toothbrush bristles) rather than by weight.

Example 4

Certain rheology characteristics of toothpastes are important for consumer acceptance. For example, it is generally desirable that a dentifrice does not separate with aging, is easy to dispense from a toothpaste tube, demonstrates good ribbon properties without strings, and distributes evenly and smoothly over the teeth. It is also desirable that the product does not dry out readily when exposed to air (as discussed in Example 5, below).

Reduced stringiness of a dentifrice composition also indicates less product retention in equipment during manufacturing, thus resulting in more efficient processing and easier cleaning/sanitizing of equipment. It also indicates cleaner product dispensing from the tube and less messy cap/orifice buildup over time.

In order to quantify stringiness of a toothpaste composition, a sample of the toothpaste was loaded into a cup held in a fixed position and a probe was lowered into the sample. More specifically, the cup was 7 mm deep and 24 mm wide, the probe was a Nylon ball, 16 mm in diameter, and the initial gap between the ball and the bottom of the cup was 4 mm. After 1 min rest, the probe is raised out of the toothpaste sample at a steady rate. The point at which the toothpaste ribbon stretched between the sample in the cup and the probe breaks is then recorded. This experiment was done at 25° C. Table 9 shows resulting stringiness values of optimized formulas described in Table 7. The data is an average of three measurements at both 10 mm/sec and 30 mm/sec separation speeds. As can be seen, the compositions of the present invention display significantly reduced stringiness compared to the benchmark.

TABLE 9

Toothpaste Stringiness Measurements

| | Formula (from Example 3) | | | | | |
|---|---|---|---|---|---|---|
| | P | Q | R | S | T | Benchmark #1 |
| Breakup Time (Sec) @ 10 mm/sec | 1.59 | 1.42 | 1.39 | 1.89 | 1.37 | 2.24 |
| Breakup Time (Sec) @ 30 mm/sec | 0.68 | 0.63 | 0.55 | 0.78 | 0.59 | 1.17 |

Example 5

A rheology test has also been developed to quantify toothpaste dry-out when exposed to air. Dry-out is represented by an increase in relative elastic modulus over time as measured by a surface probe. More specifically, the surface probe is a de Nouy ring (R1 01 by Kruss) and it is mounted on a TA ARG2 rheometer with an attachment (supplied by TA Instruments) for surface rheology. In this evaluation, a test sample was deposited on the rheometer Peltier plate at 30° C. using a plastic bounding ring and leveled with a spatula so as to form a layer 71 mm in diameter and 6 mm in height. Then the de Nouy ring was descended on the sample so as to be positioned exactly on the surface. Oscillatory torque of 10 μN·m was applied at 1 Hz frequency and surface elastic modulus, G', was recorded as a function of time for 10 minutes. The relative increase of G' (defined as the value of G' after 10 minutes compared to its initial value) for Formula P and for the Benchmark composition are shown in Table 10, below. A lower value of Relative Increase of G' indicates less product dry-out. In these tests, Formula P (from Example 3, above) exhibits reduced product dry-out compared to the benchmark toothpaste (which contains 40 weight % PCC abrasive). This is an important advantage as calcium carbonate formulations in general tend to exhibit rapid dry-out if consumers are not vigilant in closing the cap of the toothpaste tube after usage. Product that has dried can become more difficult to dispense due to increased viscosity and may result in other sources of consumer dissatisfaction due to loss of flavor and increased mess due to cracked/crumbling product.

TABLE 10

Toothpaste Dry-out Measurements

| Formula (from Example 3) | Relative increase of G' |
|---|---|
| Benchmark | 4.3 |
| Formula "P" | 2.4 |

Example 6

Microcrystalline cellulose (MCC) was also evaluated as an additional structuring agent in combination with thickening silica and NaCMC in the high water calcium carbonate toothpaste compositions of the present invention, in order to determine potential synergistic benefits. It is believed that microcrystalline cellulose (MCC) may enhance particulate mouthfeel and flavor release attributes in high water content compositions.

Initial evaluations explored MCC for structuring capabilities, as compared to thickening silica. Microcrystalline cellulose sold under the tradename Avicel® (from FMC Corporation) was used in the experiments below. Avicel® is a spray-dried blend of MCC and NaCMC. The water-insoluble MCC provides a structured dispersion vehicle while the CMC facilitates aqueous dispersion and serves as a protective colloid. Avicel® RC-951 contains 8.3-13.8 weight % NaCMC and Avicel® CL-611 contains 11.3-18.8 weight % NaCMC. Technical information from the supplier (FMC) indicates that MCC (Avicel®) particles in water will swell and are peptidized under shear conditions to form a lattice network of cellulose microcrystals to provide structuring capabilities. The lattice network of cellulose microcrystals provides a synergistic benefit combined with the intertwined network of CMC polymer chains (the CMC being delivered with MCC as part of the Avivel® composition, and also as separately-added CMC) to increase toothpaste viscosity and yield stress. It was determined that Avicel® CL-611 was preferred due to ease of processing/dispersing and for cost considerations as compared to Avicel® RC-591. However, when aiming to provide low-cost formulations, it is noted that there may be an upper limit for the concentration levels of the Avicel® material which are practicable in such formulations, as this material is considerably more costly than NaCMC and thickener silica.

As an initial experiment, the potential of Avicel® as a replacement for NaCMC type 7 in a calcium carbonate/thickener silica toothpaste composition was evaluated (Table 11). It can be seen that up to 2 weight % Avicel® does not provide adequate viscosity and/or static yield stress properties to assure physical stability of the toothpaste.

TABLE 11

Comparison of Avicel in place of NaCMC in Toothpaste

| | Formula | | |
|---|---|---|---|
| | U | V | W |
| Ppt. Calcium Carbonate - PCC | 22.00 | 22.00 | 22.00 |
| Avicel CL-611 | 0.00 | 1.00 | 2.00 |
| Thickener Silica | 8.00 | 8.00 | 8.00 |
| NaCMC Type 7/500T | 1.00 | 0.00 | 0.00 |
| Sorbitol, N.C. (70 wt. % aq soln) | 0.00 | 0.00 | 0.00 |
| Glycerin, vegetable - USP | 9.10 | 9.10 | 9.10 |
| Tetrasodium Pyrophosphate | 1.25 | 1.25 | 1.25 |
| Sodium Bicarbonate | 0.25 | 0.25 | 0.25 |
| Sodium Silicate (1:3.26-41BE) | 0.00 | 0.00 | 0.00 |
| Sodium Hydroxide (50 wt. % aq Sol'n) | 0.23 | 0.23 | 0.23 |
| NaMFP - USP | 1.10 | 1.10 | 1.10 |
| Sodium Lauryl Sulfate | 1.76 | 1.76 | 1.76 |
| Sodium Saccharin | 0.25 | 0.25 | 0.25 |
| Flavor | 0.85 | 0.85 | 0.85 |
| Benzyl Alcohol | 0.30 | 0.30 | 0.30 |
| Demineralized Water | 53.91 | 53.91 | 52.91 |
| Viscosity (×10,000 cps)/YS (Pa) @ RT, V74 spindle | | | |
| Initial | 28/129 | 6/10 | 11/22 |
| 1 day | 30/170 | 16/12 | 14/22 |
| 3 days | 35/193 | 18/12 | 20/29 |
| 1 Week | 38/193 | 20/12 | 29/23 |
| 1 Month | 40/215 | 17/9 | 26/23 |
| Separation Score | | | |
| | 2.80 (Pass) | 4.40 (Fail) | 3.84 (Fail) |

Example 7

MCC was also evaluated as a supplement to the NaCMC/thickener silica structuring agents in calcium carbonate toothpaste compositions of the present invention to determine potential synergistic or additive benefits. In these formulations, MCC does appear to provide synergistic behavior. Concentrations of 0.5 weight % Avicel® CL-611 (which delivers 0.057-0.094 weight % NaCMC) and 1 weight % Avicel® CL-611 (which delivers 0.113-0.188 weight % NaCMC) provide desirable increases in static yield stress and product physical stability. The data in Table 12, below, suggests that the results are superior to equivalent formulas which contain no MCC, but which have a concentration of NaCMC type 7 which is greater than that provided by the addition of 0.5 or 1 weight % Avicel® CL-611 to a 1 weight % NaCMC-containing composition (for example, comparing Formulas X and Y, below, with Formula Q which contains 22 weight % PCC/8 weight % thickening silica/1.25 weight % NaCMC).

Since the compositions are typically made at the manufacturing site as a common base for later finishing (up to several days later) with different flavors and aesthetics, it is most desirable that the common base compositions provide low viscosity within the first several days of making, so that the bulk product can be easily transferred/pumped in the post-addition finishing process. For this reason, an Avicel® dosage of about 0.5 weight % (formula X) would be optimal.

TABLE 12

Avicel in PCC/Thickener Silica Toothpaste

| | Formula | | | |
|---|---|---|---|---|
| | U | X | Y | Benchmark#2 |
| Ppt. Calcium Carbonate - PCC | 22.00 | 22.00 | 22.00 | 41.00 |
| Avicel CL-611 | 0.00 | 0.50 | 1.00 | 0.00 |
| Thickener Silica | 8.00 | 8.00 | 8.00 | 0.00 |
| NaCMC Type 7/500T | 1.00 | 1.00 | 1.00 | 1.00 |
| Sorbitol, N.C. (70 wt. % aq soln) | 0.00 | 0.00 | 0.00 | 0.10-1.00 |

TABLE 12-continued

Avicel in PCC/Thickener Silica Toothpaste

| | Formula | | | |
|---|---|---|---|---|
| | U | X | Y | Benchmark#2 |
| Glycerin, vegetable - USP | 9.10 | 9.10 | 9.10 | 12.00-18.00 |
| Tetrasodium Pyrophosphate | 1.25 | 1.25 | 1.25 | 0.25-0.75 |
| Sodium Bicarbonate | 0.25 | 0.25 | 0.25 | 0.25-0.75 |
| Sodium Hydroxide (50 wt. % aq Sol'n) | 0.23 | 0.23 | 0.23 | 0.05-0.50 |
| NaMFP - USP | 1.10 | 1.10 | 1.10 | 1.00-1.50 |
| Sodium Lauryl Sulfate | 1.76 | 1.76 | 1.76 | 1.00-2.00 |
| Sodium Saccharin | 0.25 | 0.25 | 0.25 | 0.10-1.00 |
| Flavor | 0.85 | 0.85 | 0.85 | 0.95 |
| Benzyl Alcohol | 0.30 | 0.30 | 0.30 | 0.10-1.00 |
| Demineralized Water | 53.91 | 53.41 | 52.91 | 30.00-40.00 |
| Viscosity (×10,000 cps)/YS (Pa) @ RT, V74 spindle | | | | |
| Initial | 28/129 | 34/193 | 36/193 | 22/118 |
| 1 day | 30/170 | 37/213 | 48/255 | 32/257 |
| 3 days | 35/193 | 40/235 | 53/290 | 40/290 |
| 1 Week | 38/193 | 42/235 | 64/315 | 45/290 |
| 1 Month | 40/215 | 44/255 | 72/315 | 48/290 |
| Sepatation Score | | | | |
| | 2.80 (Pass) | 2.77 (Pass) | 2.65 (Pass) | 2.68 (Pass) |

In an evaluation by an expert flavorist, compositions U, X and Y with 0, 0.5 and 1 weight % Avicel®, respectively, were found to not be significantly different in terms of flavor release and overall mouthfeel. However, it was found that the compositions exhibited significantly enhanced foaming generation and density with increasing Avicel concentration (see Table 13).

TABLE 13

Foaming attributes of formulas U, Q, X and Y

| | U | Q | X | Y | Benckmk#2 |
|---|---|---|---|---|---|
| Foaming Attributes (SITA Foam Test) | | | | | |
| Foam Volume (ml) | 169 | 172 | 198 | 221 | 175 |
| Foam Stability/Decay (ml) | 220 | 232 | 237 | 255 | 195 |

The foam properties of Formulas U, Q (containing 1.25 weight % NaCMC but no MCC), X and Y were quantified by means of an in-vitro lab test called a SITA foam tester (model R-2000, manufactured by SITA Messtechnik GmbH). The instrument provides automated agitation of diluted toothpaste preparations to mimic dilution and mechanical action experienced during brushing and has been found to correlate well with sensory ratings by expert (trained) panelists. The SITA foam tester quantifies foam generation and decay utilizing an array of needles that monitor changes in electroconductance. Changes in foam volume are reported by the instrument at predetermined time intervals up to 1 minute after a pre-determined amount of agitation has been applied to the test solution (for example, the foam volume is measured every 5 seconds, with the agitation being temporarily stopped while the measurement takes place). Similarly, foam decay is measured at predetermined time intervals up to one minute but with no further agitation of the solution (i.e. the foam decay measurement starts after the 1 minute of agitation). The results in Table 13 are reported for peak foam volume during foam generation and foam volume after one minute of decay. Without wishing to be bound by any theory, it is believed that foam volume is lower for these examples during the SITA agitation process than during foam decay due to the agitation partially breaking down the foam, which then re-builds somewhat in a delayed fashion after agitation is stopped (possibly due to the settling of ingredients which may disrupt the foam structure).

250 milliliters of a solution of 4:1 water:toothpaste (by weight) was used for all SITA tests, and a stir blade rotating at 800 rpm provided agitation. The foam volume was measured at time t=0 and then at 5 second intervals up to 60 seconds total time (with the agitation being temporarily stopped while the measurements took place). The data in Table 13 indicates that there is an increase in foam generation and stability with increasing concentration of Avicel®. It can also be seen from Table 13 that the foam generation and stability of both formulas X and Y is greater than for formula Q, even although formula Q contains a higher total concentration of NaCMC compared to formulas X and Y when accounting for the maximum concentration of NaCMC which can be provided by the Avicel® in formulas X and Y.

Example 8

Expert sensory panel experiments were carried out, comparing compositions of the present invention (in two different flavor systems) with other low-cost options and also with the benchmark 40-41 weight % PCC anti-cavity formula as described in Tables 1 to 8, above (comprising 40 weight % PCC/0 weight % thickener silica/0.8 weight % NaCMC), in order to compare sensorial attributes of the compositions with those of the benchmark. The compositions of the present invention used in these tests were: formula U as discussed in Tables 11 and 12, above; and a composition comprising 22 weight % PCC/8 weight % thickener silica/1 weight % NaCMC, which corresponded to formula U but with a different type and concentration of flavor. A formulation comprising 20 weight PCC/8 weight % thickener silica/1.15 weight % NaCMC/13 weight % sorbitol; and a formulation comprising 20 weight % PCC/8 weight % thickener silica/1.25 weight % NaCMC/18 weight % glycerin were also tested. The results showed that the compositions of the present invention had no significant downsides on key sensory attributes (flavor, foam, mouthfeel and aftertaste) as compared to the benchmark 40-41 weight % PCC anti-cavity formula.

Also, a home-use test was fielded in Brazil to optimize the flavor system of a 20 weight % PCC/8 weight % thickener silica/1.1 weight % NaCMC composition (correlating to formula M, above, but with different flavor and saccharin levels). The sequential monadic study amongst 90 Brazil consumers revealed that the formulation of the present invention with 15% flavor reduction as compared to the flavor content of the 40 weight % PCC "benchmark" composition received parity ratings to the benchmark formula (90% confidence level, one-tail) on overall liking, flavor liking and other key hedonic attributes such as foam volume, flavor intensity and clean mouthfeel.

What is claimed is:

1. An oral care composition comprising, based on the total weight of the composition:
   (a) 20 to 22 weight % calcium carbonate;
   (b) 1 to 1.5 weight % sodium carboxymethyl cellulose thickening agent;
   (c) 8 to 9 weight % thickening silica; and
   (d) at least 40 weight % water,
   and
   wherein the ratio of thickening silica to water is from 1:5 to 1:8.5 by weight.

2. The oral care composition of claim 1, wherein the calcium carbonate comprises natural calcium carbonate.

3. The oral care composition of claim 1, wherein the calcium carbonate comprises precipitated calcium carbonate.

4. The oral care composition of claim 1, wherein the composition further comprises a cellulose ether thickening agent selected from the group consisting of, hydroxymethylcellulose, hydroxyethylcellulose or derivatives thereof, hydroxypropylcellulose or derivatives thereof, hydroxypropylmethylcellulose or derivatives thereof, and mixtures thereof.

5. The oral care composition of claim 1, further comprising microcrystalline cellulose.

6. The oral care composition of claim 5, comprising from 0.4 to 0.9 weight % microcrystalline cellulose.

7. The oral care composition of claim 5, wherein the ratio of microcrystalline cellulose to sodium carboxymethyl cellulose thickening agent is from 1:1 to 1:3 by weight.

8. The oral care composition of claim 7, wherein the ratio of microcrystalline cellulose to sodium carboxymethyl cellulose thickening agent is from 1:1.5 to 1:2.75 by weight.

9. The oral care composition of claim 1, comprising about 22 weight % calcium carbonate, about 1.1 weight % sodium carboxymethylcellulose, about 8 weight % thickening silica, and about 0.4 weight % microcrystalline cellulose, based on the total weight of the composition.

10. The oral care composition of claim 1, comprising about 20 weight % calcium carbonate, about 1.25 weight % sodium carboxymethylcellulose, and about 8 weight % thickening silica, based on the total weight of the composition.

11. The oral care composition of claim 1, further comprising a preservative.

12. The oral care composition of claim 11, wherein the preservative is selected from benzyl alcohol and parabens.

13. The oral care composition of claim 11, wherein the preservative is present in an amount of from 0.1 to 1 weight %, based on the total weight of the composition.

14. The oral care composition of claim 1, further comprising a humectant.

15. The oral care composition of claim 14, wherein the humectant is selected from sorbitol, glycerin, xylitol, polyethylene glycol, propylene glycol, and combinations thereof.

16. The oral care composition of claim 15, wherein the humectant is sorbitol.

17. The oral care composition of claim 15, wherein the humectant is glycerin.

18. The oral care composition of claim 14, wherein the humectant is present in an amount of from 5 to 20 weight %, based on the total weight of the composition.

19. The oral care composition of claim 1, wherein the composition has a pH of from 9.2 to 10.2.

20. The oral care composition of claim 19, wherein the composition further comprises a buffer system, the buffer system being:
  (a) a combination of sodium silicate and tetrasodium pyrophosphate;
  (b) a combination of sodium hydroxide, sodium bicarbonate and tetrasodium pyrophosphate; or
  (c) a combination of sodium bicarbonate and sodium carbonate.

21. The oral care composition of claim 20, wherein the buffer system is 0.25 to 0.75 weight % sodium silicate and 0.25 to 0.75 weight % tetrasodium pyrophosphate, based on the total weight of the composition.

22. The oral care composition of claim 20, wherein the buffer system is 0.04 to 0.5 weight % sodium hydroxide, 0.25 to 0.75 weight % sodium bicarbonate and 0.25 to 1.5 weight % tetrasodium pyrophosphate.

23. The oral care composition of claim 1, wherein the composition is a toothpaste, a tooth gel, or a combination thereof.

24. The oral care composition of claim 1, wherein the viscosity of the composition is from 100,000 to 1,000,000 cps as measured at 25° C. at 1 rpm using a Brookfield Viscometer Model HADV-II+Pro and a V74 spindle.

25. The oral care composition of claim 1, wherein the composition has a static yield stress of at least 50 Pa as measured at 25° C. using a Brookfield Viscometer Model HADV-II+Pro and a V74 spindle.

* * * * *